(12) United States Patent
Miyakawa et al.

(10) Patent No.: US 8,208,982 B2
(45) Date of Patent: Jun. 26, 2012

(54) EVANESCENT CATHETER SYSTEM

(75) Inventors: Atsuo Miyakawa, Shizuoka (JP); Matsuyuki Doi, Shizuoka (JP); Seiji Yamamoto, Shizuoka (JP); Susumu Terakawa, Shizuoka (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 1425 days.

(21) Appl. No.: 11/720,398

(22) PCT Filed: Dec. 1, 2005

(86) PCT No.: PCT/JP2005/022069
§ 371 (c)(1),
(2), (4) Date: May 29, 2007

(87) PCT Pub. No.: WO2006/059672
PCT Pub. Date: Jun. 8, 2006

(65) Prior Publication Data
US 2008/0275325 A1 Nov. 6, 2008

(30) Foreign Application Priority Data
Dec. 1, 2004 (JP) ................. P2004-348482

(51) Int. Cl.
*A61B 5/1455* (2006.01)
(52) U.S. Cl. .............. 600/317; 600/310; 600/323
(58) Field of Classification Search .............. 600/310, 600/317, 322, 326, 327, 329, 342, 473, 476; 385/12; 422/82.11
See application file for complete search history.

(56) References Cited

U.S. PATENT DOCUMENTS

| | | | |
|---|---|---|---|
| 5,146,521 A * | 9/1992 | Hartog | 385/12 |
| 5,349,954 A * | 9/1994 | Tiemann et al. | 600/342 |
| 5,399,866 A | 3/1995 | Feldman et al. | |
| 5,833,603 A * | 11/1998 | Kovacs et al. | 600/317 |
| 2004/0215134 A1 * | 10/2004 | Soykan et al. | 600/322 |

FOREIGN PATENT DOCUMENTS

| | | |
|---|---|---|
| EP | 1 294 186 | 3/2003 |
| JP | 3278164 | 12/1991 |

(Continued)

OTHER PUBLICATIONS

Search Report Corresponding to International Application No. PCT/JP2005/022069, Mailed Dec. 27, 2005.

(Continued)

*Primary Examiner* — Eric Winakur
*Assistant Examiner* — Chu Chuan (JJ) Liu
(74) *Attorney, Agent, or Firm* — Greenlee Sullivan P.C.

(57) ABSTRACT

An evanescent catheter system having a tip portion of an optical fiber capable of securely measuring fluorescence intensity or fluorescence spectrum of a substance around a catheter tip, without being hindered by optical absorption of hemoglobin in erythrocytes in blood, and being capable of calculating an existing amount of a fluorescence-emitting substance existing in an evanescent light generating part. A protecting layer 22 and a cladding 23 are removed from an upper semicircular part of a core 24 at a tip of a catheter 21 to expose the core 24. When excitation light 29 is incident, evanescent light 25 is generated on the upper semicircular part of the core 24 and a fluorescent substance generates emits fluorescence 30. An interference filter 26 filters out the excitation light and only the fluorescence 30 reaches the photodiode 28, permitting a measuring device to measure an existing amount of the fluorescent substance.

6 Claims, 11 Drawing Sheets

FOREIGN PATENT DOCUMENTS

| | | |
|---|---|---|
| JP | 4-221743 | 8/1992 |
| JP | H10-002905 | 1/1998 |
| JP | 2000-516719 | 12/2000 |
| JP | 2002-214132 | 7/2002 |
| JP | 3429282 | 7/2003 |
| WO | WO 03/005890 | 1/2003 |

OTHER PUBLICATIONS

Supplementary European Search Report, Corresponding to European Application No. EP 05 81 1430, Completed Jun. 25, 2009.

* cited by examiner

EVANESCENT CATHETER SYSTEM

CROSS-REFERENCE TO RELATED APPLICATIONS

This application is the U.S. National Stage of International Application No. PCT/JP2005/022069, filed Dec. 1, 2005, which claims the benefit of Japanese Patent Application P2004-348482, filed Dec. 1, 2004, both of which are hereby incorporated by reference to the extent not inconsistent with the disclosure herewith.

TECHNICAL FIELD

The present invention relates to evanescent catheters with an optical fiber having the tip thereof placed in blood, which are adapted to introduce excitation light into the fiber and to detect fluorescence from a fluorescent substance excited thereby and, more particularly, to catheter systems taking account of an evanescent light generating structure at the catheter tip and a structure capable of securely receiving fluorescence from a fluorescent substance.

BACKGROUND ART

One of the conventional methods of measuring or detecting a concentration change in blood or the like is to take a sample of blood, separate blood cells by a blood cell separator film, a centrifugal separator, or the like, and thereafter determine the quantity of components except for the blood cells by an ordinary method.

On the other hand, when the quantity is directly determined from the interior of blood, the hemoglobin existing in the erythrocytes absorbs light in a wide wavelength band during the detection of fluorescence from a fluorescent substance (pharmaceutical agent or the like) injected into the blood, and with many pharmaceutical agents, it is thus difficult to avoid the influence of optical absorption of the hemoglobin. There are only few pharmaceutical agents the quantity of which can be determined without the influence of optical absorption of the hemoglobin.

Incidentally, Patent Document 1 (automated system and sample analysis method) discloses an optical method of utilizing fiber-optic evanescent light to detect an organic substance contained in blood or the like. This method is to remove a cladding layer of an optical fiber forming a light-detection sensor so as to generate evanescent light in a surface of the core layer, to immerse this part in a liquid sample such as the blood, to receive detected fluorescence from the liquid sample with the light-detection sensor, and to detect an organic substance in the liquid sample such as the blood through an optical addressing module.

Furthermore, Patent Document 2 (light detecting device) discloses a light detecting device utilizing an optical fiber (guide) and arranged to bring a liquid sample (blood or the like) into contact with the optical guide, to excite a light emitting substance in the evanescent field, and to measure it by a photoelectric detector.

The foregoing Patent Documents 1, 2 both enable the selective and quantitative measurement of the light emitting composition in the blood or the like by use of evanescent light, but in cited Document 1 the optical illumination system for generating the evanescent light on the film of the core by removing the cladding at the tip of the optical fiber is a popular structure and its light-receiving optical system is composed of a reflected feedback path of the optical fiber. Cited Document 2 describes that the evanescent light is generated on the surface of the optical guide and the light receiving system is the photoelectric detector provided separately on the other end side of the optical guide. Patent Documents 1, 2 both are directed in common to the technology of separately taking the liquid sample and determining the quantity.

Therefore, their configurations are unable to determine the quantity within a living organism and the erythrocytes must be separated in advance according to need in order to eliminate the influence of the hemoglobin in blood.

Important portions for implementing the determination of quantity without the influence of hemoglobin within a living organism are configurations of the illumination system and light receiving system at the tip of the optical fiber, but Patent Documents 1, 2 fail to disclose the details of special structure about the tip of optical fiber.

Now let us focus our attention to systems in which the illumination system and light receiving system are formed by sharpening the core part at the tip of optical fiber, and Patent Documents 3, 4, and 5 disclose the tip structural portions of optical fiber.

Patent Document 3 (fiber-optic sensor for measurement of absorption spectrum using total reflection, and system thereof) discloses the following technology: a part of the cladding of the optical fiber is removed as shown in FIG. 1 of Patent Document 3, a sensor part using evanescent light by total reflection is provided at the tip of the optical fiber, this sensor part is inserted into a living organism so as to bring the sensor part into direct contact with a living tissue, the evanescent light is generated at the sensor part by a light wave having propagated as repeatedly totally reflected, the evanescent light is absorbed by a chemical component of the living tissue in contact with the sensor part to change its spectrum, it is reflected by a totally reflecting film, it is again absorbed by the chemical component, and the reflected light thereof is returned through the optical fiber.

This is the technology of measuring the absorption spectrum in the living tissue, but is not to detect fluorescence from a fluorescent substance in blood. It eliminates propagation in the living tissue, thus avoids multiple scattering due to propagation to minimize the influence of scattering, and improves the accuracy of the absorption spectrum with spatial resolution.

The configuration near the cladding part at the tip of the optical fiber in cited Document 3 is one for adapting the intensity of evanescent light generated outside the cladding part to the intensity of incident light, and is able to capture a spectral change of the evanescent light varying as absorbed by the chemical component in the living tissue. It is, however, unable to capture fluorescence emitted in the region where the evanescent light is generated outside the optical fiber, by the optical fiber and to return it to the entrance side.

Patent Document 4 (optical fiber and production method thereof) describes the shape of an optical probe of a near-field optical microscope for detecting the existence of a chemical substance or the like including the blood or the like in a living tissue and, as shown in FIGS. 1, 2, 5, 7, and 8 of Patent Document 4, the core is projected in a conical shape at the tip from the cladding, and a light shield film is formed on the core and cladding surface of the projecting part except for an opening part at the tip.

The optical fiber probe of this structure is arranged to condense light by providing the light shield film on the core part of conical shape of the projecting part as well to enhance the evanescent field generated in the surface of the detection end of the core to improve the detection sensitivity.

However, since scattered light by a sample in the evanescent field is made incident into the opening part at the tip with a very small surface area as shown in FIG. 11 of Patent Document 4, it is disadvantageous in terms of collection of scattered light in a wide area and the total increase of received light power is considered to be small. Furthermore, it is not a device that directly detects the intensity of fluorescence from a fluorescent substance in a living tissue.

Furthermore, Patent Document 5 (optical fiber and production method thereof) describes an optical fiber used in a photon scanning microscope or the like for detecting the evanescent light localized in a region smaller than the wavelength of light in a surface of a substance; the optical fiber has the structure in which one end of the core is sharpened in a tapered shape, a light-shielding coating layer is formed on the surface of the sharpened core, and an opening part is formed so as to expose the tip end; light is made incident and emergent through the other end of this optical fiber; the light incident through the end of the optical fiber is condensed at the tapered portion and is projected from the opening part to the outside. This makes the evanescent light generated and scattered in proximity of the surface of the substance, and this scattered light is guided through the opening part into the core to be outputted from the other end of the optical fiber.

This configuration solved the problem of the conventional technology that the cladding diameter was much longer than the length of the detection end and the peripheral part of the cladding could collide with the surface of the sample to break the sample or the tip of the optical probe, and thereby enhances the detection efficiency of the optical probe, while preventing the peripheral part of the cladding from colliding with the surface of the sample.

This configuration is also the shape similar to that in Patent Document 4, and it is thus disadvantageous in terms of collection of scattered light and the increase of received light power is considered to be small, as described above.

Patent Document 1: Japanese Patent No. 3429282
Patent Document 2: Published Translated Version of PCT Application No. 2000-516719
Patent Document 3: Japanese Patent Application Laid-Open No. 2002-214132
Patent Document 4: Japanese Patent Application Laid-Open No. 10-2905
Patent Document 5: Japanese Patent No. 3278164

DISCLOSURE OF THE INVENTION

Object to be Achieved by the Invention

The present invention has been accomplished in order to solve the above-described various problems, and an object of the invention is to provide an evanescent catheter system in which a catheter with an optical fiber utilizing evanescent light, has a structure of an optical fiber tip portion capable of securely measuring a fluorescence intensity or fluorescence spectrum of a substance around the tip of the catheter, without being hindered by optical absorption of the hemoglobin in erythrocytes, and which is capable of measuring an existing amount of a fluorescence-emitting substance existing in an evanescent light generating part.

Means for Achieving the Object

In order to achieve the above object, claim 1 of the present invention is an evanescent catheter system adapted to place in blood an optical fiber obtained by removing a cladding layer to expose a core layer, to generate evanescent light, to detect fluorescence from a fluorescent substance excited by the evanescent light, and to measure an existing amount of the substance in the blood on the basis of a fluorescence intensity, wherein substantially a half of the cladding covering the core is removed at a columnar tip of the optical fiber whereby the evanescent light is generated on an upper columnar surface of the core, and wherein an optical filter for transmitting the fluorescence in a predetermined wavelength region is located on a lower columnar surface of the core exposed by removing the cladding layer, a light receiving element is located on a back side of the optical filter, and the light receiving element detects the fluorescence from the fluorescent substance.

Claim 2 of the present invention is an evanescent catheter system comprising a first optical fiber for transmitting excitation light, and a second optical fiber for receiving fluorescence, and adapted to place in blood an optical fiber obtained by removing a cladding layer of the first optical fiber to expose a core layer, to generate evanescent light, to receive fluorescence from a fluorescent substance excited by the evanescent light, by the second optical fiber, and to measure an existing amount of the substance in the blood on the basis of a fluorescence intensity, wherein substantially a half of the cladding layer covering the core is removed at a columnar tip of the first optical fiber whereby the evanescent light is generated on an upper columnar surface of the core, and wherein a reflecting mirror is located in the second optical fiber opposed to the core resulting from the removal of substantially the half of the cladding, and the reflecting mirror reflects the fluorescence from the fluorescent substance to guide the fluorescence to an output end of the second optical fiber.

Claim 3 of the present invention is an evanescent catheter system adapted to place in blood an optical fiber obtained by removing a cladding layer to expose a core layer, to generate evanescent light, to detect fluorescence from a fluorescent substance excited by the evanescent light, and to measure an existing amount of the substance in the blood on the basis of a fluorescence intensity, wherein the cladding layer is removed from an entire circumference of the core in a predetermined range at a columnar tip of the optical fiber, an inclined surface is formed from a top toward a root of a tip of the core part from which the cladding layer is removed, and a reflecting mirror is located on the inclined surface to generate the evanescent light on a columnar upper surface of the cladding-removed core, and wherein the reflecting mirror reflects the fluorescence from the fluorescent substance to guide the fluorescence to an output end of the optical fiber.

Claim 4 of the present invention is an evanescent catheter system adapted to place in blood an optical fiber obtained by removing a cladding layer to expose a core layer, to generate evanescent light, to detect fluorescence from a fluorescent substance excited by the evanescent light, and to measure an existing amount of the substance in the blood on the basis of a fluorescence intensity, wherein substantially a half of the cladding covering the core is removed at a columnar tip of the optical fiber, the evanescent light is generated on a columnar upper surface of the core exposed after the removal of the cladding, and a large number of reflecting mirrors are arranged so as to be inclined at a predetermined inclination angle relative to the optical axis, on a lower columnar surface of the cladding-removed core, whereby the large number of reflecting mirrors are arranged to reflect the fluorescence from the fluorescent substance to guide the fluorescence to an output end of the optical fiber.

Claim 5 of the present invention is an evanescent catheter system adapted to place in blood an optical fiber obtained by removing a cladding layer to expose a core layer, to generate evanescent light, to detect fluorescence from a fluorescent substance excited by the evanescent light, and to measure an existing amount of the substance in the blood on the basis of a fluorescence intensity, wherein the core part from which the cladding layer is removed at a columnar tip of the optical fiber, is formed in such a conical shape as to make a predetermined angle relative to the optical axis, whereby the evanescent light is generated on a surface of the core part of the conical shape, and wherein the core part of the conical shape reflects the fluorescence from the fluorescent substance to guide the fluorescence to an output end of the optical fiber.

Claim 6 of the present invention is an evanescent catheter system adapted to place a tip of an optical fiber in blood, to generate evanescent light, to detect fluorescence from a fluorescent substance excited by the evanescent light, and to measure an existing amount of the substance in the blood on the basis of a fluorescence intensity, wherein a protecting layer of the cladding layer is removed from a columnar tip of the optical fiber and the core in the cladding layer is formed in a spiral shape, wherein excitation light leaking from the core of the spiral shape reaches a columnar surface of the cladding layer to generate the evanescent light on the columnar surface of the cladding layer, and wherein the core part of the spiral shape reflects the fluorescence from the fluorescent substance to guide the fluorescence to an output end of the optical fiber.

Effect of the Invention

According to the above configurations, the evanescent light is generated in the vicinity of the core layer, i.e., about 0.1 μm in the surface of the core layer, the erythrocytes have the size of several μm, and the molecular size, for example, of riboflavin, propofol, or bilirubin as a fluorescent substance is of nm order which is 1/1000 or less of the size of the erythrocytes; therefore, there is little influence of the hemoglobin in the erythrocytes, and the fluorescence from the fluorescent substance excited by the evanescent light can be securely detected. Since this fluorescence intensity is dependent on the mass of the fluorescent substance existing in the evanescent light generating part, the existing amount of the fluorescence emitting substance such as riboflavin can be calculated based on the fluorescence intensity.

Figure 1:
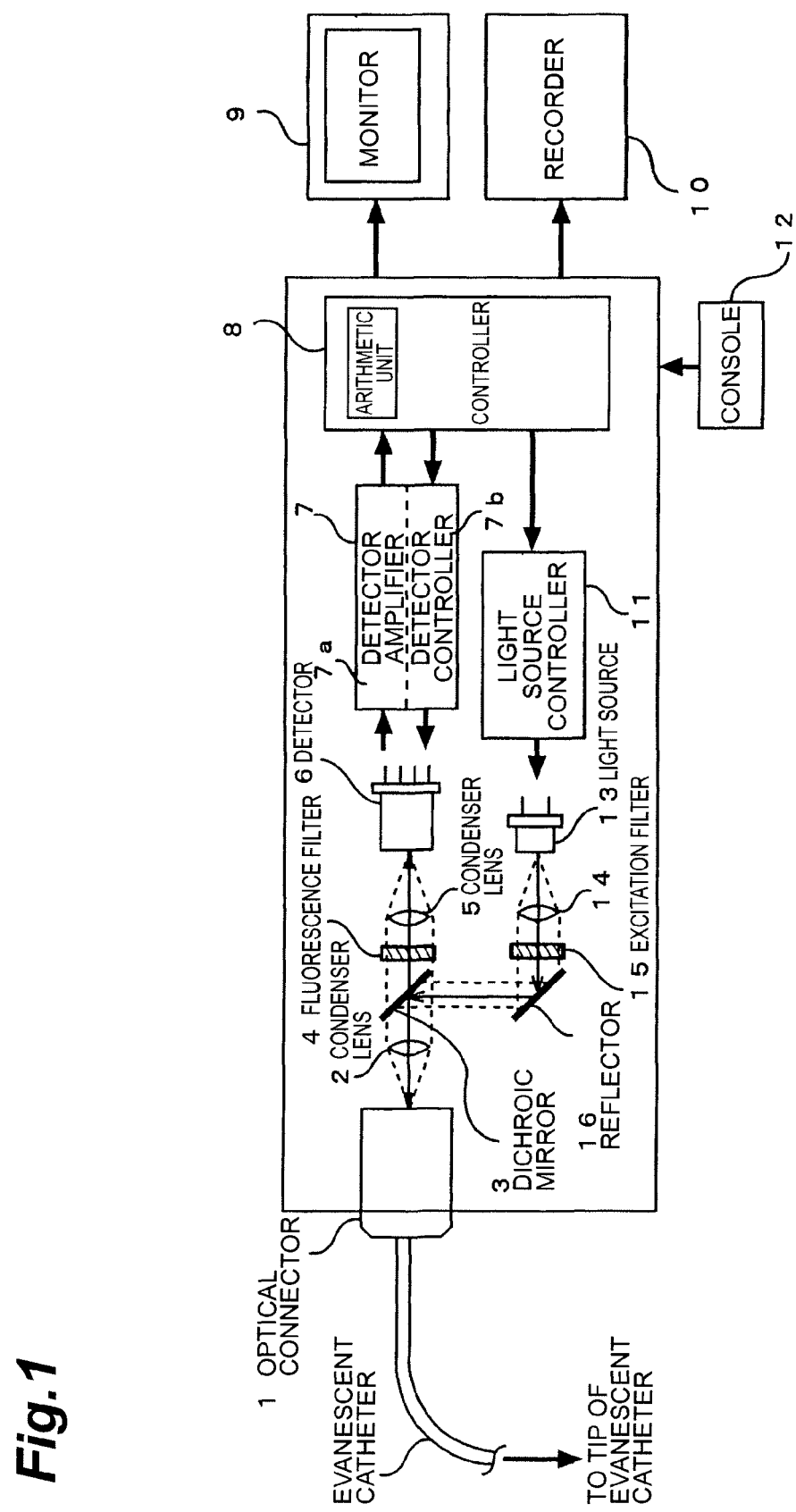
FIG. 1 is a drawing showing a configuration example of an evanescent catheter system according to the present invention, which is applied to the third, fourth, fifth, and sixth embodiments of the structure of the catheter tip.

DESCRIPTION OF REFERENCE SYMBOLS 1 optical connector
2, 5, 14, 18 condenser lenses
3 dichroic mirror
4 fluorescence filter
6 detector (photodiode or the like)
7 detector amplifier-detector controller
8 controller
9 monitor
10 recorder (X-Y plotter)
11 light source controller
12 console control unit
13 light source (semiconductor laser, LED, xenon lamp, or the like)
15 excitation filter
16, 19 reflecting mirrors
21, 31, 41, 51, 61, 71 catheters
22, 32, 72 protecting layers
23, 33, 43, 53, 63, 73 claddings
24, 34, 44, 54, 64, 74 cores
25, 35, 45, 55, 65, 75 evanescent light
26 optical filter
27, 37, 47, 57, 77 reflecting mirrors
28 photodiode
29, 38, 48, 58, 68, 79 excitation light
30, 39, 49, 59, 69, 80 fluorescence

BEST MODES FOR CARRYING OUT THE INVENTION

Embodiments of the present invention will be described below in detail with reference to the drawings.

FIG. 1 is a drawing showing a configuration example of an evanescent catheter system according to the present invention.

This example is a configuration diagram of an optical system and circuit system applied to the catheter structures of the third, fourth, fifth, and sixth embodiments (FIG. 6, FIG. 7, FIG. 8, and FIG. 9).

A controller 8 feeds a control signal for activation of a light source to a light source controller 11 on the basis of an instruction from a console control unit 12. The light source controller 11 activates a light source 13 such as a semiconductor laser or a xenon lamp. Excitation light from the light source 13 passes through a condenser lens 14 and an excitation filter 15 and is reflected by a reflecting mirror 16 and a dichroic mirror 3 to be guided to an optical fiber end of optical connector 1 by condenser lens 2. The excitation light incident through the optical fiber end is transmitted to the tip of the evanescent catheter.

Fluorescence from the tip of the evanescent catheter is outputted from the same optical fiber end, passes through the condenser lens 2 and dichroic mirror 3, and further travels through a fluorescence filter (band-pass filter) 4, which is located behind the dichroic mirror 3 and which transmits fluorescence, and through a condenser lens 5 to enter a photodetector 6 such as a photomultiplier or a photodiode.

In order to select an excitation wavelength and a fluorescence wavelength suitable for a fluorescent substance to be measured, it is also possible to provide a plurality of semiconductor lasers or LEDs with different emission wavelengths, and to attach a mechanism for manually or automatically replacing the excitation filter or the fluorescence filter with another, though not shown.

The photodetector 6 receives an activation signal and a timing signal from detector controller 7b to move into a fluorescence detectable state. The fluorescence (in a predetermined wavelength region) detected by the photodetector 6 is converted into an electric signal, which is amplified by detector amplifier 7a.

The controller 8 performs the light source control and measurement operation by an arithmetic element such as a CPU on the basis of a control program, performs A/D conversion of a received output from the amplifier 7a, and calculates a fluorescence intensity on the basis of a predetermined equation. Then it calculates an existing amount of a fluorescent substance in blood on the basis of the fluorescence intensity.

A monitor 9 displays a menu screen for the measurement operation and also displays the measured fluorescence intensity and the existing amount of the fluorescent substance. The specs such as the output of the light source and the wavelength region are displayed in the menu screen, and an operator is allowed to perform adjustment such as selection of the emission wavelength and output of the light source, and the fluorescence filter by means of the console control unit 12. It is also possible to adjust the arithmetic contents to be outputted.

A recorder 10 records a change in intensity of fluorescence from the fluorescent substance such as riboflavin in blood with time.

Since a semiconductor laser emits monochromatic light, there is no need for provision of a band-pass filter such as an excitation filter on the light source side in that case.

Although not shown, it is also possible to attach an injection tubule, a balloon inflation pipe, or the like to the evanescent catheter.

Since many intravital substances and pharmaceutical agents fluoresce, there are a large number of substances that can be targets as fluorescent substances. Examples of the targets include the following materials.

Intravital substances; bilirubin, B-complex vitamins, etc.

Pharmaceutical agents; propofol, riboflavin, indocyanine green, etc.

The pharmaceutical agents are often injected into a living body by an intravenous injection. There are some types of pharmaceutical agents introduced by an intramuscular injection or peroral administration (pills) to implement measurement of an in-blood concentration change.

The light to be injected into the optical fiber, i.e., the light to generate evanescent light is excitation light for the fluorescent substance (riboflavin, indocyanine green, or the like) as a target. Specifically, the excitation light for riboflavin is light around 450 nm, and the excitation light for indocyanine green is light around 750 nm. The term "around" means light in an excitation wavelength band.

The light outputted from the optical fiber is of a fluorescence emission wavelength; the fluorescence by riboflavin is in a wavelength band with the peak wavelength of 525 nm; the emission by indocyanine green is in a wavelength band with the peak of 830 nm.

Next, the relation of fluorescence intensity obtained from the intensity of excitation light will be described using a calculation example.

The fluorescence intensity is expressed by the following equation:

$$I_{em} = 2.30359 \times I_{ex} \times \epsilon \times C \times \phi \tag{1}$$

where $I_{em}$: number of fluorescence photons per unit volume ($cm^3$);

$I_{ex}$: number of photons of excitation light per unit area ($cm^2$);

$\epsilon$: molar extinction coefficient of fluorescent molecules fluorescein: 90,000 $M^{-1}$ $cm^{-1}$ C: molar concentration of fluorescent molecules 1 μM $\phi$: quantum yield of fluorescent molecules fluorescein: 0.9

The fluorescein in this example has the high molar extinction coefficient and quantum yield, and many of fluorescent molecules in a living body have 1/100 or less of those. The concentration is also often much smaller than 1 μM. Therefore, the above example is an ideally best intensity calculation.

The optical fiber used has the diameter r of 0.25 mm and the length L of 10 mm in which the evanescent light is generated.

It is assumed that the intensity $F_i$ of the excitation light injected into the optical fiber is 10 mW. (Precisely, it must be expressed by the number of photons, but it is approximately expressed in units of energy because the wavelength of the excitation light is close to that of fluorescence. The same also applies to the description hereinafter.)

Therefore, the excitation light intensity per unit area $F_{ex}$ is expressed by the following equation:

$$F_{ex} = F_i/(\pi \times r^2) = 10/(3.14159 \times 0.0125^2) = 20371.8 \text{ mWcm}^{-2} \tag{2}$$

Although it depends upon the refractive indices of the core and blood, the light of this intensity is assumed to be the evanescent light.

When the thickness t of emission of the evanescent light is 100 nm (0.00001 cm), the excited volume V is represented by the following equation:

$$\begin{aligned} V &= 2 \times \pi \times r \times L \times t \\ &= 2 \times 3.14159 \times 0.0125 \times 10 \times 0.00001 \\ &= 0.00000785398 \text{ cm}^3. \end{aligned} \tag{3}$$

Therefore, by putting Eqs (2) and (3) into Eq (1), the generated fluorescence intensity $F_{em}$ is obtained as follows:

$$F_{em} = 0.0298415 \text{ mW}.$$

The intensity of the fluorescence is thus about 1/335 of the intensity of the injected excitation light.

The area of emission of evanescent light in the first embodiment of FIG. 4 described later is half of that under the above calculation conditions, and the incidence efficiency of fluorescence is considered to be approximately 30%. Therefore, approximately 1/2000 of the emitted fluorescence can be received as fluorescence. In the second to sixth embodiments of FIG. 5 and subsequent figures the incidence efficiency is worse and the received fluorescence is thus weaker.

Figure 2:
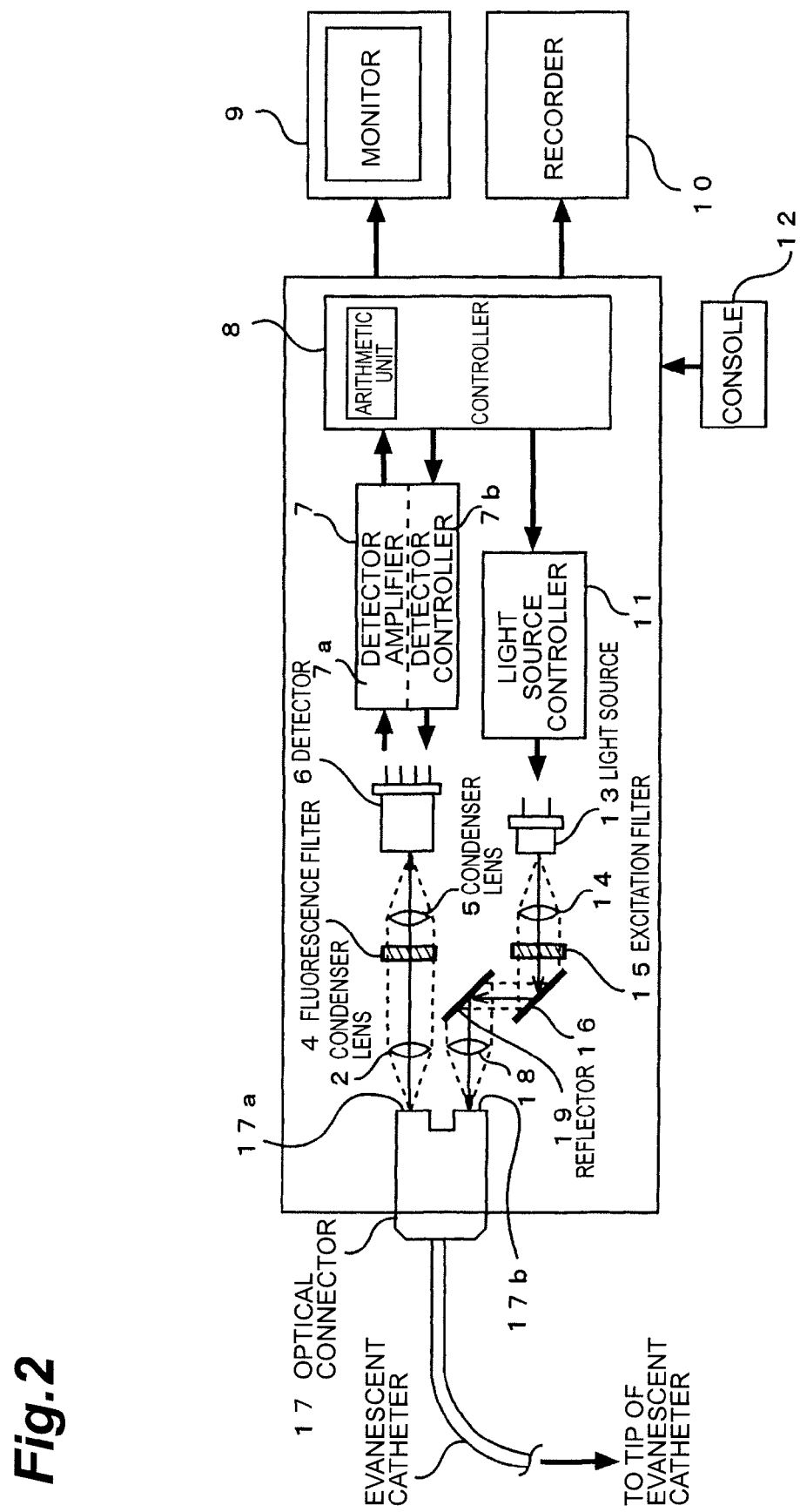
FIG. 2 is a drawing showing a configuration example of an evanescent catheter system according to the present invention, which is applied to the second embodiment of the structure of the catheter tip.

FIG. 2 is a drawing showing a configuration example of an evanescent catheter system according to the present invention, which is an example of application of the structure of the catheter tip to the second embodiment. Since this example is different from FIG. 1 in that the catheter system uses two optical fibers for injection of excitation light and for output of fluorescence, only the different structure will be described below.

There are two optical fiber ends 17a, 17b at an end of the optical connector 17, and an output optical system for receiving the fluorescence output is connected in the same manner as in FIG. 1, to the optical fiber end 17a. On the other hand, there are a condenser lens 18, reflecting mirrors 16, 19, excitation filter 15, and condenser lens 14 arranged at the optical fiber end 17b to guide the excitation light from the light source 13 such as a semiconductor laser to the optical fiber end 17b.

The reflecting mirrors 16, 19 on the light source side in this embodiment are used because the spacing between the entrance and exit of the optical connector 17 of the evanescent catheter is small; however, if the light source 13 is a compact semiconductor laser or the like, they can be omitted. Since a semiconductor laser emits monochromatic light, there is no need for use of a band-pass filter or the like for the excitation filter on the light source side in that case.

Figure 3:
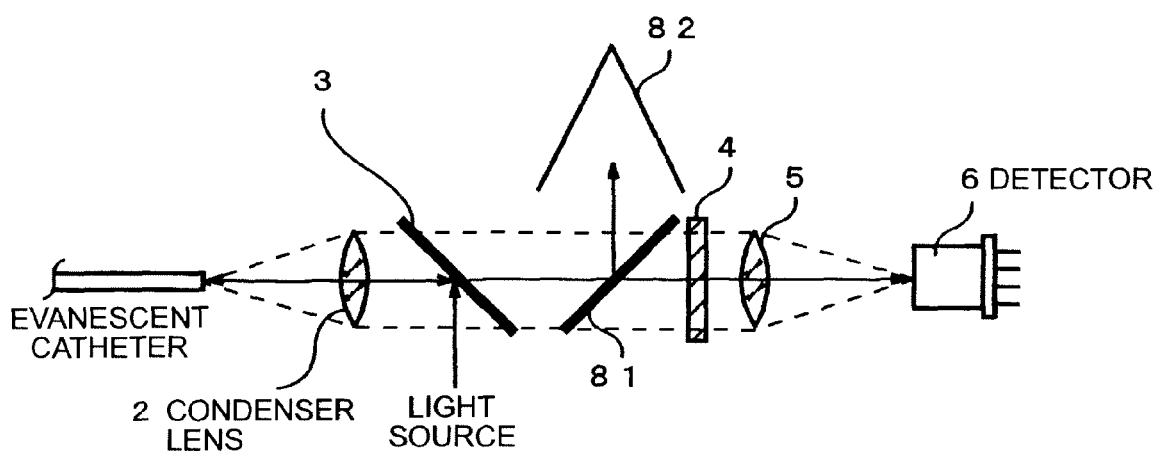
FIG. 3 is a drawing showing an example of a separation optical system for separation of excitation light and fluorescence.

FIG. 3 is a drawing showing an example of a separation optical system for separation of the excitation light and fluorescence.

A feedback beam of the excitation light is processed as follows: as shown in FIG. 3, a dichroic mirror or notch filter 81 is inserted into the light-receiving optical system to direct the excitation light toward an excitation light absorbing cone 82. The relative level of fluorescence is raised by preventing the excitation light from returning to the detector 6.

One filter as described above has substantially the attenuation rate of about $10^{-3}$-$10^{-4}$. For this reason, the measurement becomes difficult in the embodiment of the structure of FIG. 4 described later, and it is thus necessary to perform signal processing with a lock-in amplifier or the like. The embodiments of structures of FIG. 5 and subsequent figures described later need to use two or more filters to prevent the feedback of excitation light. Since it is difficult to perform practical measurement in total darkness, it is difficult to adequately remove a hindrance of external light by use of a band-pass filter which transmits only the fluorescence band, and it is thus necessary to perform signal processing with a lock-in amplifier or the like.

Embodiments of the tip part of the catheter will be described below.

Figure 4:
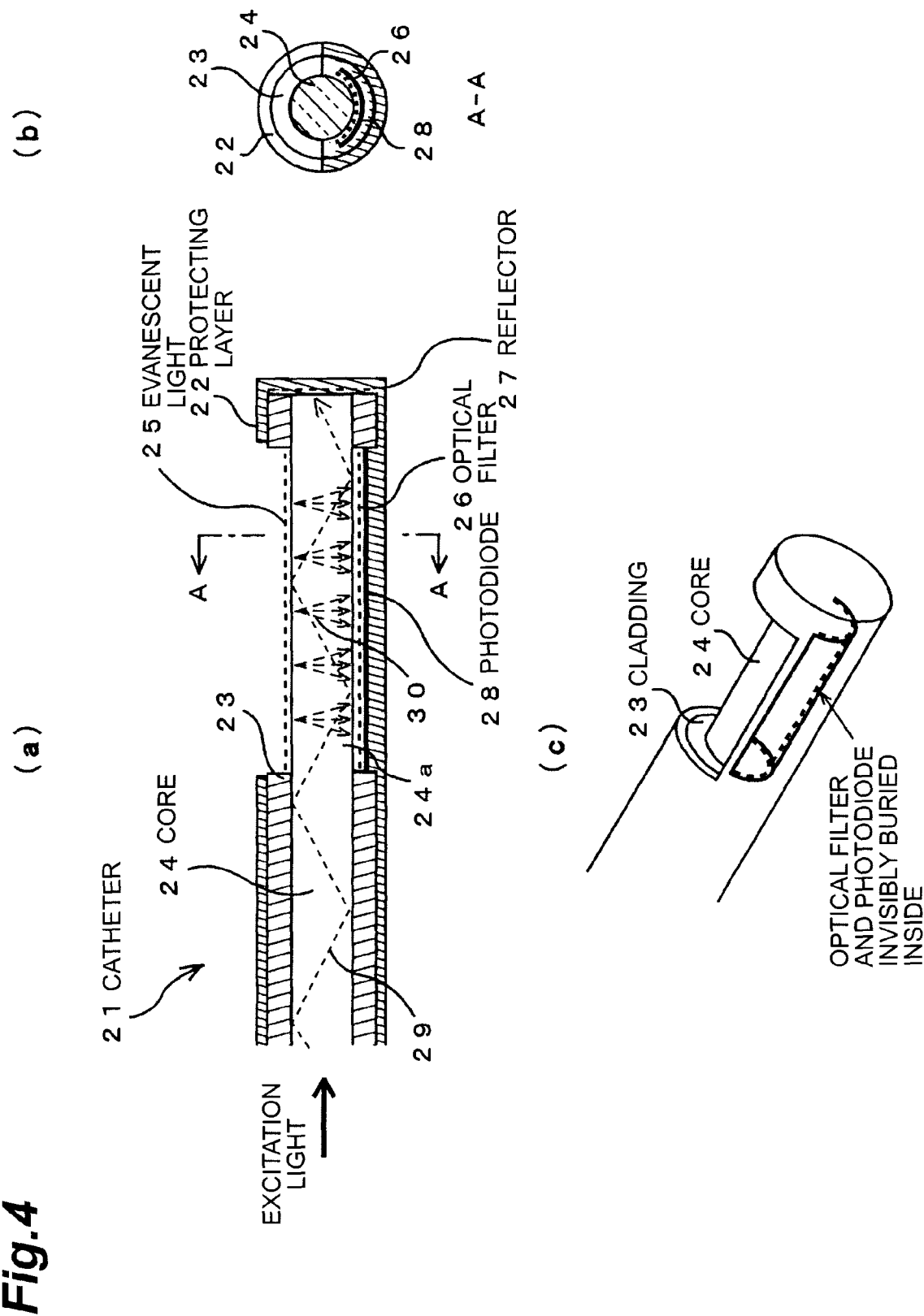
FIG. 4 is a drawing showing the first embodiment of the catheter tip part in an evanescent catheter system according to the present invention, wherein (a) shows a front sectional view, (b) a side sectional view, and (c) a perspective view.

FIG. 4 is a drawing showing the first embodiment of the catheter tip part in the evanescent catheter system according to the present invention, wherein (a) shows a front sectional view, (b) a side sectional view, and (c) a perspective view.

The catheter 21 has a structure in which a protecting layer 22 and a cladding 23 are removed across a semicircle of the optical fiber near the tip thereof. A reflecting mirror is located at the tip of the optical fiber, and it can enhance the intensity of the evanescent light and reduce a leakage of the excitation light into blood. An optical filter 26 of an arcuate shape is located opposite to the lower half of core 24a in the removed part. Furthermore, a photodiode 28 is similarly arranged in an arcuate shape on the back of the optical filter 26. An unrepresented electric cable is connected to the photodiode 28 and the electric cable is internally mounted so as to reach the other end of catheter 21.

The optical filter 26 can be, for example, an interference filter that can extract an arbitrary wavelength in a bandwidth of from several nm to several ten nm by making use of interference of light. For example, when riboflavin is used as a fluorescent substance, the filter 26 transmits a wavelength region of the band from several nm to several ten nm centered on 525 nm and filters out the other wavelengths.

The optical filter 26 is formed by the thin-film evaporation technology and the photodiode 28 of semicylindrical shape by the semiconductor fabrication technology, at the tip part of the catheter.

This embodiment requires a catheter dedicated for each measurement item, and cannot completely filter out the excitation light by the single optical filter 26; therefore, the present embodiment needs to use a lock-in amplifier inserted in the signal processing circuit after the fluorescence is received by the light receiving element.

The structure of the tip part of this catheter does not require the light-receiving optical system in the signal processing apparatus of FIG. 1 but needs the configuration of only the optical system for feeding the excitation light from the light source, and the unrepresented electric cable is led into the detector amplifier 7.

When the excitation light 29 is incident into the optical fiber, the evanescent light 25 is generated on the bared surface in the upper half of core 24. The optical filter 26 removes the excitation light 29, and the fluorescence 30 emitted by the fluorescent substance is incident to the photodiode 28.

Since this embodiment uses only one optical fiber, the profile of the catheter can be smaller and the catheter can have the size equal to or smaller than that of the ordinary catheters. A catheter for measurement of the degree of oxygen saturation usually uses two optical fibers, whereas the present embodiment uses only one optical fiber and thus can decrease the profile of the catheter. In addition, the efficiency of reception of fluorescence is high.

Figure 5:
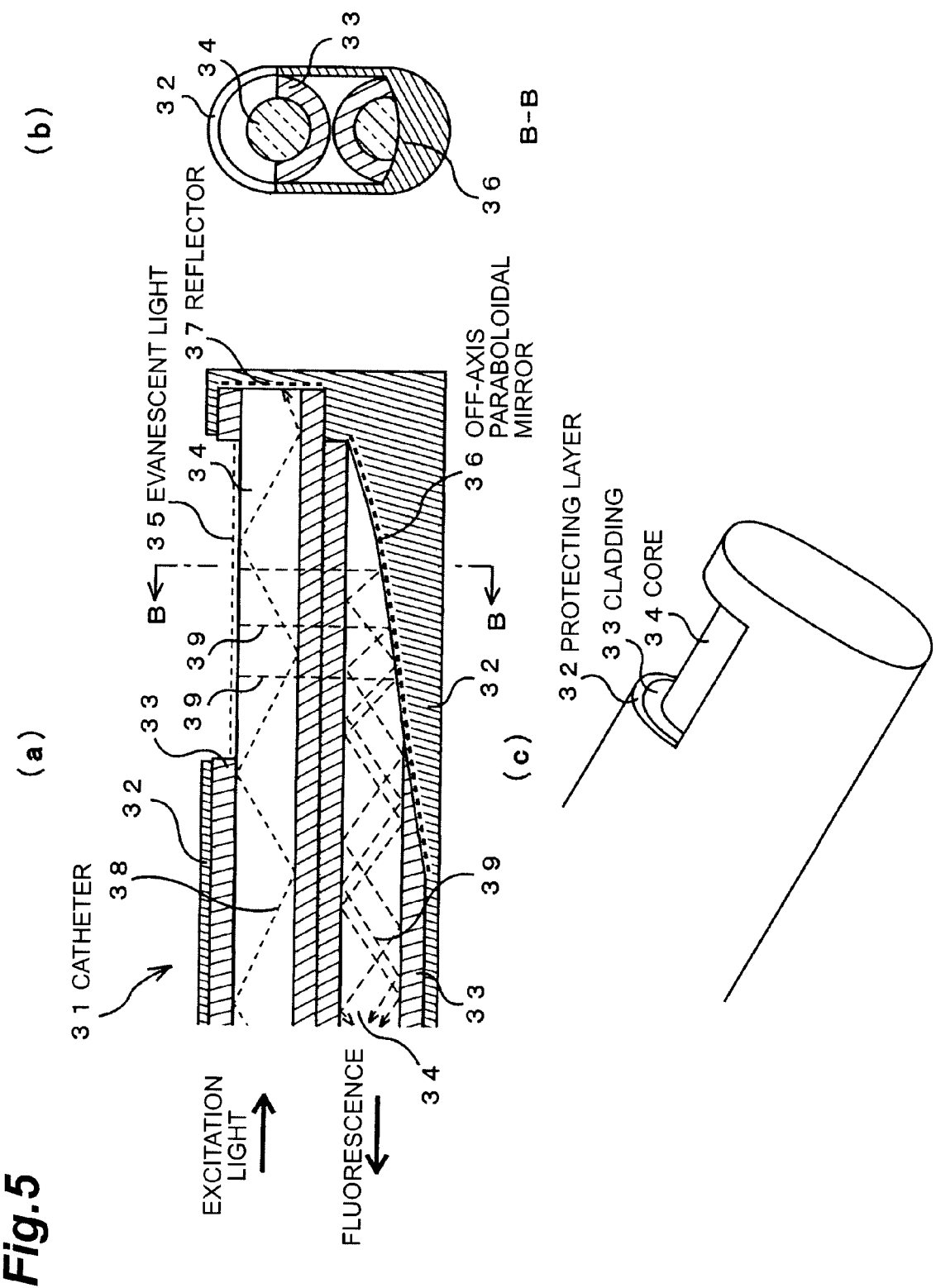
FIG. 5 is a drawing showing the second embodiment of the catheter tip part in an evanescent catheter system according to the present invention, wherein (a) shows a front sectional view, (b) a side sectional view, and (c) a perspective view.

FIG. 5 is a drawing showing the second embodiment of the catheter tip part in the evanescent catheter system according to the present invention, wherein (a) shows a front sectional view, (b) a side sectional view, and (c) a perspective view.

This embodiment uses the signal processing device of FIG. 2.

The present embodiment adopts a structure in which a protecting layer 32 and a cladding 33 are removed across a semicircular region near a tip of an optical fiber for excitation light. A reflecting mirror is located at the tip of the optical fiber to enhance the intensity of the evanescent light and to reduce a leakage of the excitation light into blood. A reflecting mirror such as an off-axis paraboloidal mirror 36 or a plane mirror is formed in a corresponding portion of another optical fiber for reception of fluorescence.

When the excitation light 38 is incident into the optical fiber for excitation light, the evanescent light 35 is generated on the bared surface in the upper half of core 34. The fluorescence 39 emitted by the fluorescent substance is reflected by the reflecting mirror to be guided to the end of the optical fiber for reception of fluorescence.

The catheter for measurement of the degree of oxygen saturation usually uses two optical fibers, while the catheter of the present embodiment has the same size and is arranged to guide the excitation light and the fluorescence through the different optical fibers; therefore, it is easy to separate the excitation light and the fluorescence. In addition, the efficiency of reception of fluorescence is also relatively high and fabrication is also easy.

Figure 6:
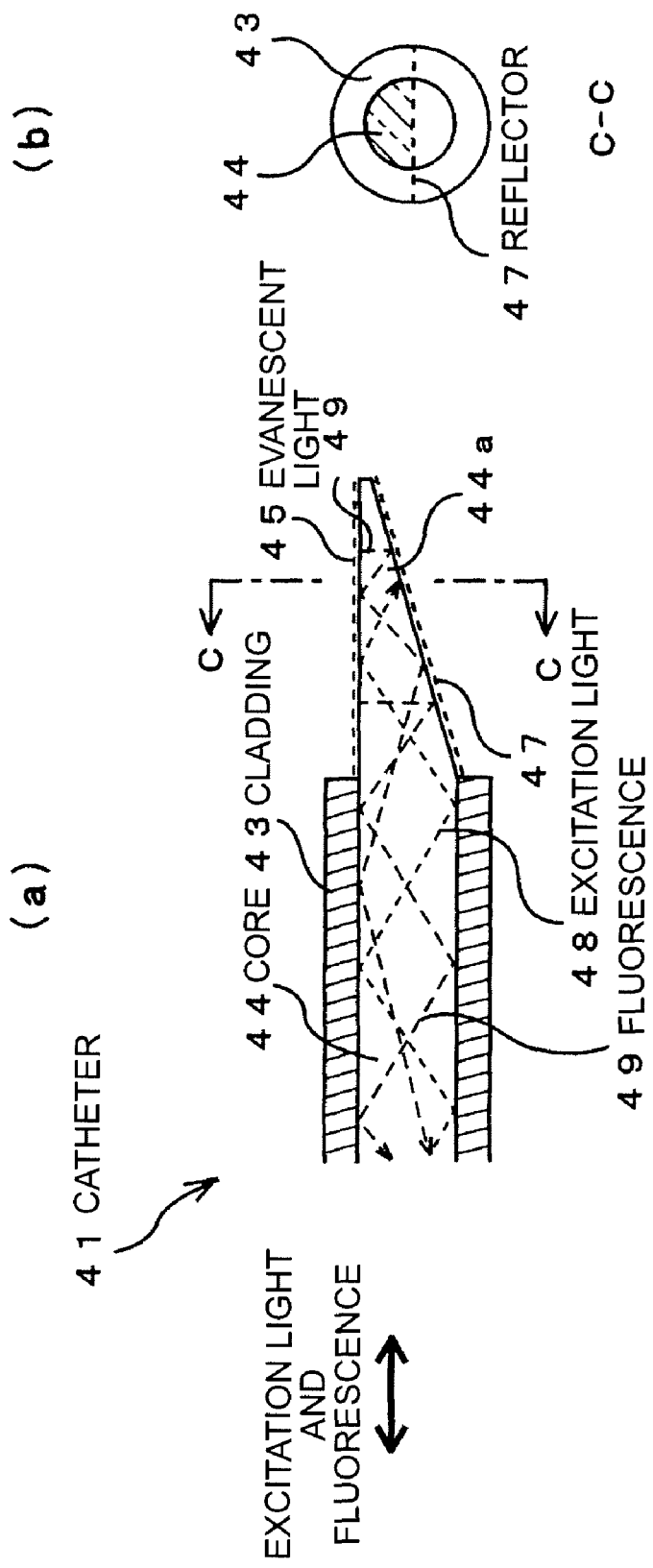
FIG. 6 is a drawing showing the third embodiment of the catheter tip part in an evanescent catheter system according to the present invention, wherein (a) shows a front sectional view and (b) a side sectional view.

FIG. 6 is a drawing showing the third embodiment of the catheter tip part in the evanescent catheter system according to the present invention, wherein (a) shows a front sectional view and (b) a side sectional view.

The cladding 43 is removed from the region near the tip part of catheter 41 and the tip part of core 44 is of a shape 44a obtained by obliquely cutting it from one edge of the columnar tip. A reflecting mirror 47 such as an off-axis paraboloidal mirror or a plane mirror is formed on the cut surface.

When the excitation light 48 is incident, the evanescent light 45 is generated on the upper surface of the core shape 44a from which the cladding 43 is removed. Fluorescence 49 emitted from the fluorescent substance as excited by the evanescent light 45 is reflected by the reflecting mirror 47 to return through the optical fiber.

Figure 7:
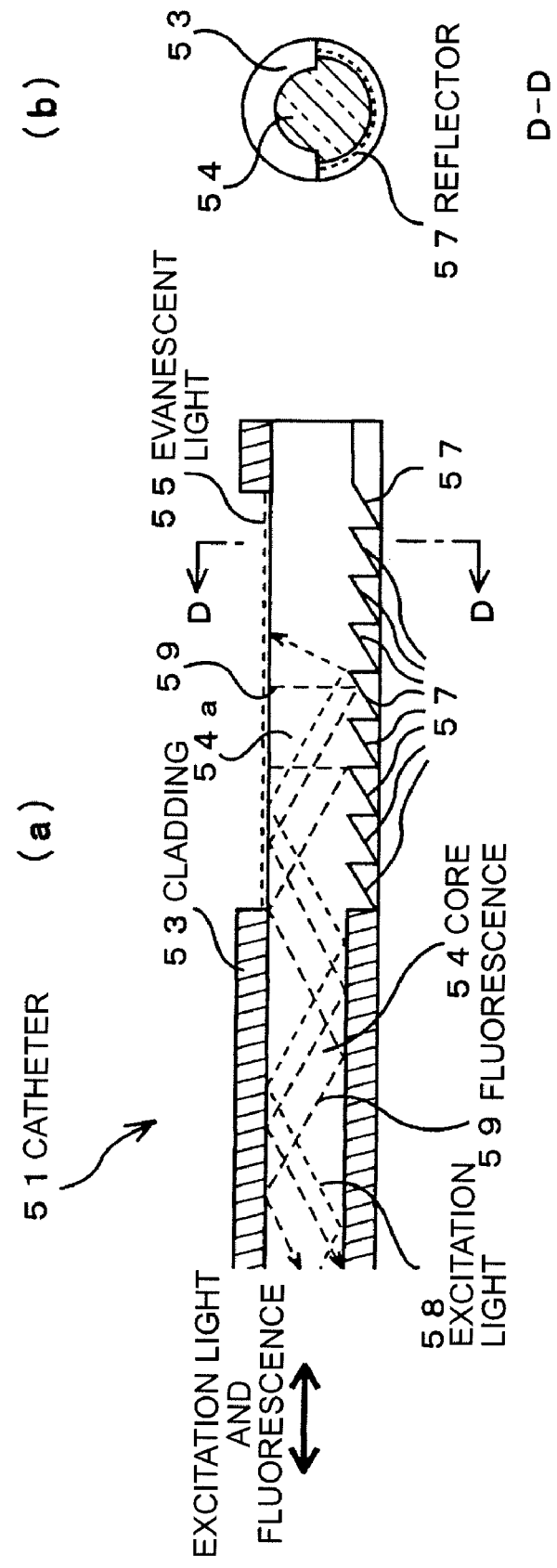
FIG. 7 is a drawing showing the fourth embodiment of the catheter tip part in an evanescent catheter system according to the present invention, wherein (a) shows a front sectional view and (b) a side sectional view.

FIG. 7 is a drawing showing the fourth embodiment of the catheter tip part in the evanescent catheter system according to the present invention, wherein (a) shows a front sectional view and (b) a side sectional view.

The catheter of the present embodiment has a structure in which the cladding 53 is removed across the upper semicircle near the tip of catheter 51. A large number of reflecting mirrors 57 of a shape similar to the Fresnel surface are formed in the surface of the lower half of the core part 54a from which the cladding 53 is removed.

When the excitation light 58 is incident, the evanescent light 55 is generated on the upper surface of core shape 54a from which the cladding 53 is removed. Fluorescence 59 emitted from the fluorescent substance as excited by the evanescent light 55 is reflected by the large number of reflecting mirrors 57 to return through the optical fiber.

The third and fourth embodiments use the signal processing device of FIG. 1.

These catheters can be made in a thin profile and fabrication thereof is easy; particularly, the third structure can be readily fabricated. However, they will experience a heavy leakage of light except for the evanescent light by virtue of influence of the reflecting mirror or mirrors. The detection area is approximately equal to that in the second embodiment but the efficiency of reception of fluorescence is low; it is thus necessary to effect adequate separation of the fluorescence signal from the excitation light in the signal processing device.

Figure 8:
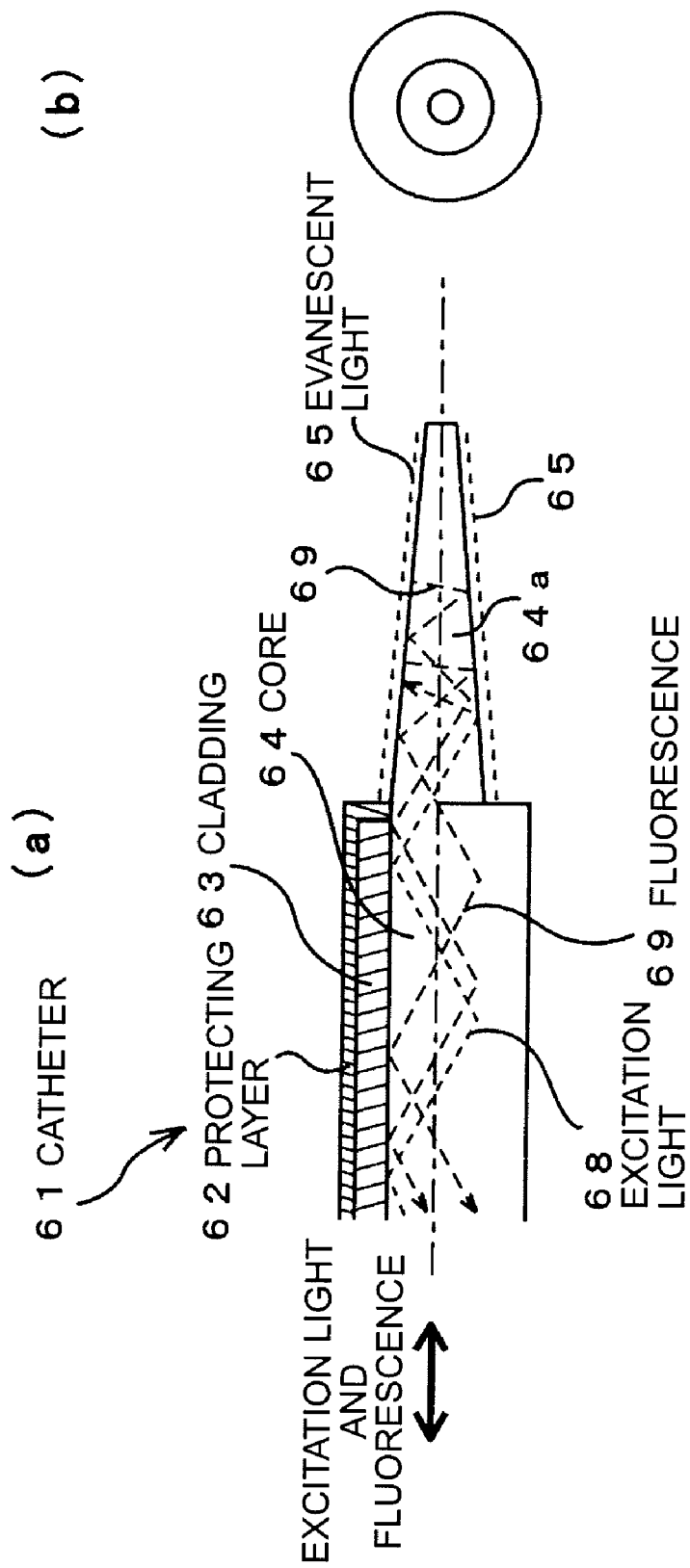
FIG. 8 is a drawing showing the fifth embodiment of the catheter tip part in an evanescent catheter system according to the present invention, wherein (a) shows a front sectional view and (b) a side view.

FIG. 8 is a drawing showing the fifth embodiment of the catheter tip part in the evanescent catheter system according to the present invention, wherein (a) shows a front sectional view and (b) a side view.

The protecting layer 62 and cladding 63 are removed from the region near the tip of catheter 61 and the core 64 is of a conical shape.

When the excitation light 68 is incident, the evanescent light 65 is generated on the entire surface of the core 64a of the conical shape. Fluorescence 69 emitted from the fluorescent substance as exited by the evanescent light 65 returns through the optical fiber.

This embodiment allows the catheter to be made in a thin profile, and facilitates the fabrication thereof. The present embodiment will experience a heavy leakage of light except for the evanescent light by virtue of the influence of the taper of the optical fiber. The detection area is narrow and the efficiency of reception of fluorescence is low; it is thus necessary to implement adequate separation of the fluorescence signal from the excitation light in the signal processing device.

Figure 9:
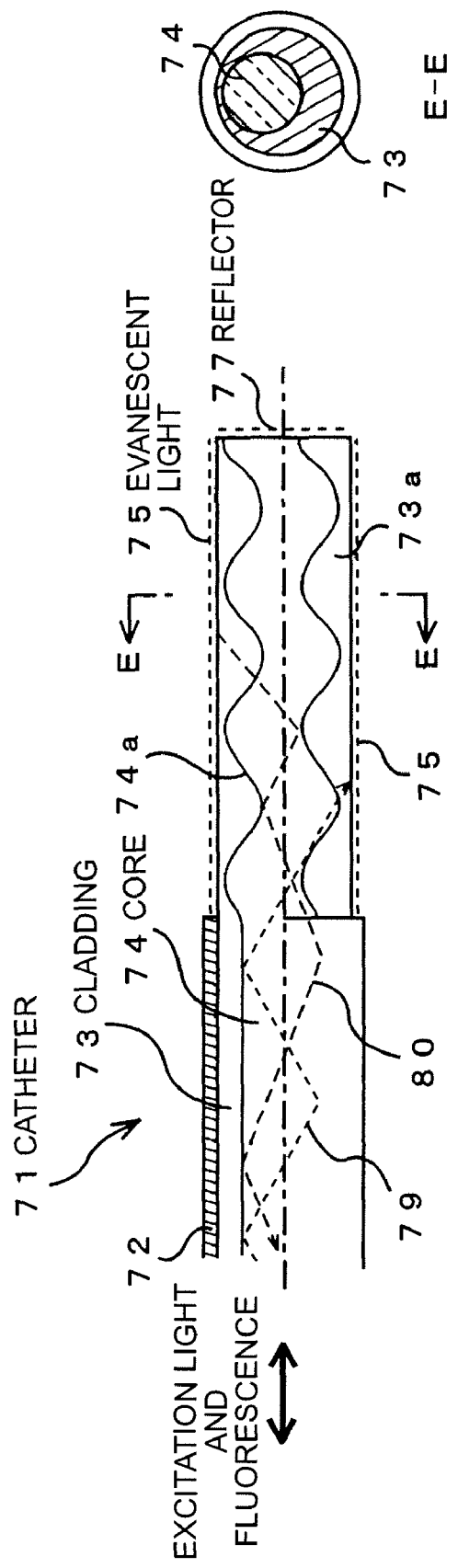
FIG. 9 is a drawing showing the sixth embodiment of the catheter tip part in an evanescent catheter system according to the present invention, wherein (a) shows a front sectional view and (b) a side view.

FIG. 9 is a drawing showing the sixth embodiment of the catheter tip part in the evanescent catheter system according to the present invention, wherein (a) shows a front sectional view and (b) a side view.

Only the protecting layer 72 is removed from the region near the tip of catheter 71 and the cladding 73a of columnar shape is exposed. The core 74 is formed in a spiral shape 74a inside this exposed tip part 73a of cladding 73. A reflecting mirror 77 is formed at the dead end of the optical fiber, which can enhance the intensity of the evanescent light and reduce a leakage of the excitation light into blood.

The excitation light 79 penetrates into the cladding 73a. This results in generating the evanescent light 75 on the surface of cladding 73a. The excitation light reflected by the reflecting mirror 77 penetrates similarly at fall faces of the corrugated shape 74a with respect to the traveling direction of excitation light 79 into the cladding 73a to generate the evanescent light 75 on the surface of cladding 73a. Fluorescence 80 emitted from the fluorescent substance as exited by the evanescent light 75 is captured in the reverse paths, by the optical fiber to return to the entrance end.

This embodiment also permits the catheter to be made in a thin profile as the above-mentioned embodiments, and can make the detection area wider than in the other embodiments. The present embodiment will experience a heavy leakage of light except for the evanescent light by virtue of influence of the meander of the optical fiber. The fabrication of the meandering optical fiber is harder than in the other embodiments. Since the feedback of the excitation light also increases, it becomes necessary to implement adequate separation of the fluorescence signal from the excitation light in the signal processing device.

Figure 10:
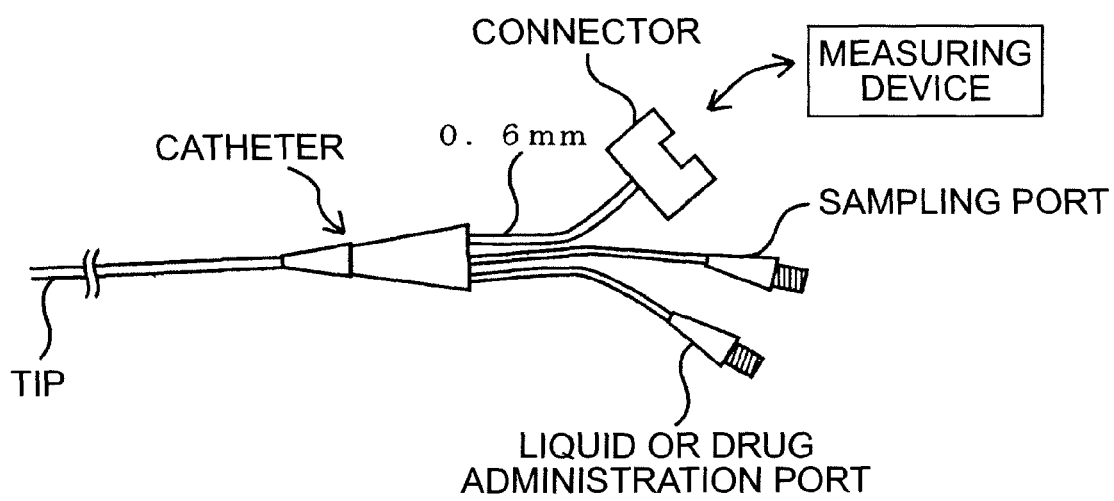
FIG. 10 is a drawing showing an example of an evanescent catheter.

FIG. 10 is a drawing showing an example of the evanescent catheter.

The catheter has a portion in which an optical fiber is inserted, a sampling port, and a liquid or drug administration port. A connector is connected to the end of the optical fiber and is connected to a measuring device as a signal processing device.

Figure 11:
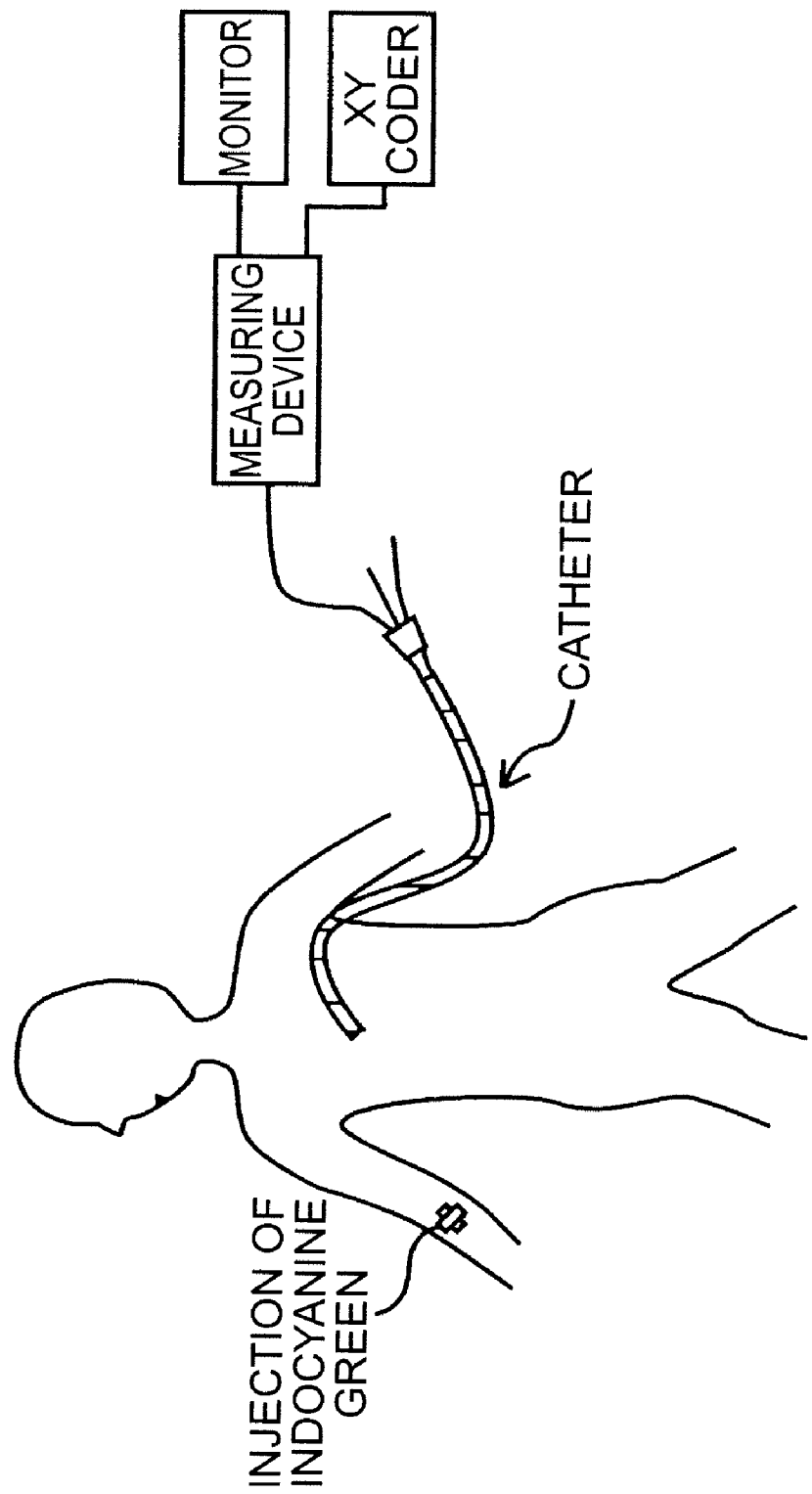
FIG. 11 is a drawing showing a system example for placing an evanescent catheter in a living tissue and measuring an existing amount of a fluorescent substance in blood.

FIG. 11 is a drawing showing a state in which the evanescent catheter is placed in a living tissue. The catheter is inserted from the root of the brachial region and the distal end thereof reaches a predetermined intravenous portion of the heart. The present invention enables measurement of an existing amount of a fluorescent substance, while reducing influence of the hemoglobin in the blood, even in the living tissue, and provides the structure of the tip part of the catheter that can obtain a measurable fluorescence output relative to the excitation light.

INDUSTRIAL APPLICABILITY

The present invention provides the catheter systems that are introduced into a living tissue in order to perform clinical inspection thereof or to monitor a pharmaceutical agent and measure an in-blood concentration change thereof or the like.

The invention claimed is:

1. An evanescent catheter system adapted to be placed in blood comprising:
   an optical fiber obtained by removing a cladding layer to expose a core layer, to generate evanescent light, to detect fluorescence from a fluorescent substance excited by the evanescent light, and to measure an existing amount of the substance in the blood on the basis of a fluorescence intensity,
   wherein substantially a half of the cladding covering the core is removed at a columnar tip of the optical fiber whereby the evanescent light is generated on an upper columnar surface of the core, and
   an optical filter for transmitting the fluorescence in a predetermined wavelength region located on an inner lower columnar surface of the core exposed by removing the cladding layer, wherein the optical filter comprises an upper side and a lower side, wherein the upper side of the optical filter is more proximal to the exposed core than the lower side, and a light receiving element is located on the lower side of the optical filter, wherein the light receiving element detects the fluorescence from the fluorescent substance.

2. The catheter system of claim 1 wherein the light receiving element is a photodiode.

3. The catheter system of claim 1 further comprising a detector amplifier able to receive output from the light receiving element.

4. The catheter system of claim 3 further comprising a controller able to receive output from the detector amplifier and calculate fluorescence intensity using the output from the amplifier.

5. The catheter system of claim 4 wherein said controller is able to calculate the existing amount of the fluorescent substance using the calculated fluorescence intensity.

6. The catheter system of claim 1 wherein the optical filter is an interference filter.

* * * * *